United States Patent
Krapcho et al.

[11] 3,948,889
[45] Apr. 6, 1976

[54] 5-[(SUBSTITUTED AMINO)ALKYL]-2-ARYL-3-HALO-1,5-BENZOTHIAZEPIN-4(5H)-ONES

[75] Inventors: John Krapcho, Somerset; Chester Frank Turk, Kendall Park, both of N.J.

[73] Assignee: E. R. Squibb & Sons, Inc., Princeton, N.J.

[22] Filed: Jan. 30, 1975

[21] Appl. No.: 545,459

Related U.S. Application Data

[62] Division of Ser. No. 462,266, April 19, 1974, Pat. No. 3,895,006.

[52] U.S. Cl. .......................................... 260/239.3 B
[51] Int. Cl.² ........................................ C07D 281/02
[58] Field of Search ............................. 260/239.3 B

[56] References Cited
UNITED STATES PATENTS 3,895,006  7/1975  Krapcho et al............... 260/239.3 B

*Primary Examiner*—Natalie Trousof
*Assistant Examiner*—Robert T. Bond
*Attorney, Agent, or Firm*—Lawrence S. Levinson; Merle J. Smith; Donald J. Barrack

[57] ABSTRACT

Benzothiazepines having the formula:

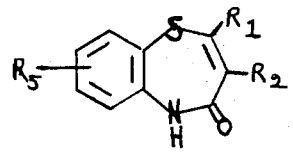

wherein $R_1$ is phenyl or substituted phenyl wherein the substituent is selected from the group consisting of alkyl, alkoxy, halogen, trifluoromethyl or alkyl

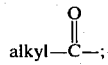

$R_2$ is chlorine or bromine; and $R_5$ is hydrogen, alkyl, alkoxy, halogen or trifluoromethyl; and wherein the terms alkyl and alkoxy, in each instance employed, refer to groups having 1 to 6 carbon atoms. These compounds are useful as intermediates in the preparation of the claimed pharmaceutically active compounds of Ser. No. 462,266, filed Apr. 19, 1974, now U.S. Pat. No. 3,895,006.

3 Claims, No Drawings

5-[(SUBSTITUTED AMINO)ALKYL]-2-ARYL-3-HALO-1,5-BENZOTHIAZEPIN-4(5H)-ONES

This application is a divisional of copending U.S. patent application Ser. No. 462,266, filed Apr. 19, 1974 now U.S. Pat. No. 3,895,006.

SUMMARY OF THE INVENTION

Compounds having the structure

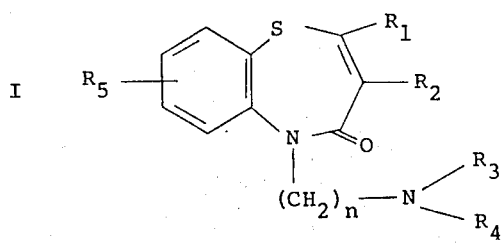

the pharmaceutically acceptable salts thereof, the quaternary ammonium salts thereof, and the sulfoxide and sulfonyl derivatives thereof, have useful antidepressive activity. In formula I, and throughout the specification, the symbols are as defined below.

$R_1$ can be phenyl or phenyl substituted with alkyl, alkoxy, halogen, trifluoromethyl or

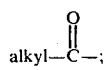

$R_2$ can be chlorine or bromine;

$R_3$ can be hydrogen, alkyl, or phenylalkyl;

$R_4$ can be alkyl;

$R_5$ can be hydrogen, alkyl, alkoxy, halogen, or trifluoromethyl; and $n$ is 2, 3, or 4.

The term "alkyl" as used throughout the specification refers to straight and branched chain alkyl groups having 1 to 6 carbon atoms, e.g., methyl, ethyl, propyl, isopropyl, butyl, t-butyl, pentyl, hexyl, and the like. Alkyl groups having 1 to 3 carbon atoms are preferred.

The term "alkoxy" as used throughout the specification refers to groups having the formula alkyl-O—, wherein alkyl is as defined above.

The term "halogen" refers to fluorine, chlorine, bromine, and iodine; chlorine and bromine are the preferred halogens.

The preferred phenylalkyl groups are benzyl and phenylethyl.

DETAILED DESCRIPTION OF THE INVENTION

The compounds of this invention are prepared using as starting materials 2,3-dihydro-2-aryl-1,5-benzothiazepine-4(5H)-ones having the structure

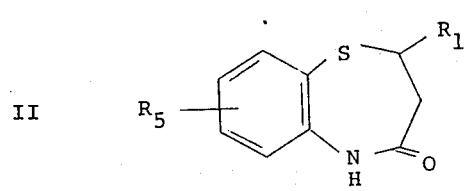

The starting materials of formula II are known; see, for example, U.S. Pat. No. 3,075,967.

A chlorine or bromine atom can be introduced into the 3-position of a benzothiazepine of formula II by reaction of the benzothiazepine with N-chloro or N-bromosuccinimide. The reaction can be run in an organic solvent, preferably a polar organic solvent such as dimethylformamide. Reaction conditions are not critical, but the reaction should be run at an elevated temperature of from about 70° to 110°C for about 1 to 8 hours. The resulting 3-halo-2-aryl-1,5-benzothiazepin-4(5H)-ones have the structure

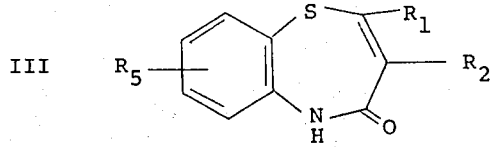

Compounds of formula I can be prepared by reacting the appropriate 3-halo-2-aryl-1,5-benzothiazepin-4(5H)-one of formula III with an amine salt having the structure

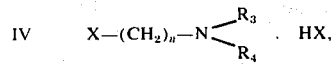

wherein X is chlorine or bromine. The reaction can be carried out in an organic solvent, e.g., benzene, toluene, xylene, etc., in the presence of a strong base, e.g., sodium hydroxide. Reaction conditions are not critical, and the reaction will usually be carried out with heating.

In some instances it is advantageous to introduce the basic side chain onto a compound of formula III by a two step procedure. A compound of formula III is first reacted with a compound having the structure

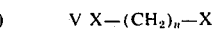

to yield an intermediate having the structure

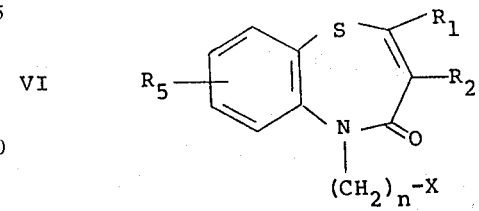

Reaction of an intermediate of formula VI with an amine having the formula

VII 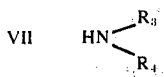

yields the compounds of formula I. The reaction can be run in an inert solvent such as toluene, at an elevated temperature. Optionally, a catalyst such as sodium iodide can be present.

Compounds of formula I wherein $R_1$ is phenyl are preferred.

Compounds of formula I wherein $R_3$ is alkyl are preferred.

Compounds of formula I wherein $R_5$ is hydrogen are preferred.

Compounds of formula I wherein $n$ is 2 or 3 are preferred.

The compounds of formula I form acid addition salts with inorganic and organic acids. These acid addition salts frequently provide useful means for isolating the products from reaction mixtures by forming the salt in a medium in which it is insoluble. The free base may then be obtained by neutralization, e.g., with a base such as sodium hydroxide. Any other salt may then be formed from the free base and the appropriate inorganic or organic acid. Illustrative are the hydrohalides, especially the hydrochloride and hydrobromide which are preferred, sulfate, nitrate, phosphate, borate, acetate, tartrate, maleate, citrate, succinate, benzoate, ascorbate, salicylate, methanesulfonate, benzenesulfonate, toluenesulfonate and the like.

The sulfoxide and sulfonyl derivatives of the compounds of formula I can be prepared using techniques well known in the art. Oxidation of a compound of formula I using hydrogen peroxide yields the corresponding sulfoxide derivative. Oxidation of a compound of formula I using potassium permanganate yields the corresponding sulfonyl derivative. Alternatively, the sulfoxide and sulfonyl derivatives can be prepared by treating compounds of formula I with m-chloroperbenzoic acid. Treating a compound of formula I with an equivalent of m-chloroperbenzoic acid for from 2 to 24 hours at room temperature yields the corresponding sulfoxide derivative. Treating a compound of formula I, or a sulfoxide derivative of a compound of formula I, with two equivalents of m-chloroperbenzoic acid for 2 to 24 hours at room temperature (or for a shorter time with slight heating) yields the corresponding sulfonyl derivative.

The compounds of formula I form quaternary ammonium salts with alkyl halides (e.g., methyl chloride, isobutyl bromide, dodecyl chloride and cetyl iodide), benzyl halides (e.g., benzyl chloride), and dialkyl sulfates (e.g., dimethyl sulfate).

The compounds of formula I, the pharmaceutically acceptable salts thereof, the quaternary ammonium salts thereof, and the sulfoxide and sulfonyl derivatives thereof, are useful for relieving depression (particularly endogenous depression) in mammals, in a manner similar to imipramine, when administered in a daily dose of from 0.5 to 3 mg/kg, preferably 1 to 2 mg/kg. The compounds of this invention reverse tetrabenazine-induced ptosis in the mouse.

The compounds of the present invention can be administered orally, for example, with an inert diluent or with an assimilable edible carrier, or they can be enclosed in hard or soft gelatin capsules, or they can be compressed into tablets, or they can be incorporated directly with the food of the diet. For oral therapeutic administration, the active compounds of this invention can be incorporated with excipients and used in the form of tablets, troches, capsules, elixirs, suspensions, syrups, wafers, chewing gum, and the like. Such compositions and preparations should contain at least 0.1% of active compound. The percentage in the compositions and preparations can, of course, be varied and can conveniently be between about 5 to about 75% or more of the weight of the unit. The amount of active compound in such therapeutically useful compositions or preparations is such that a suitable dosage will be obtained. Preferred compositions or preparations according to the present invention are prepared so that an oral dosage unit form contains between about 5 and 250 milligrams of active compound.

The tablets, troches, pills, capsules and the like can also contain the following: a binder such as gum tragacanth, acacia, corn starch or gelatin; and excipient such as dicalcium phosphate; a disintegrating agent such as corn starch, potato starch, alginic acid and the like; a lubricant such as magnesium stearate; and a sweetening agent such as sucrose, lactose or saccharin or a flavoring agent such as peppermint, oil or wintergreen, or cherry flavoring. When the dosage unit form is a capsule, it can contain in addition to materials of the above type a liquid carrier such as a fatty oil. Various other materials can be present as coatings or to otherwise modify the physical form of the dosage unit; for instance, tablets, pills, or capsules can be coated with shellac, sugar, or both. A syrup or elixir can contain the active compounds, sucrose as a sweetening agent, methyl and propyl parabens as preservatives, a dye and a flavoring such as cherry or orange flavor. Of course, any material used in preparing any dosage unit form should be pharmaceutically pure and non-toxic in the amounts employed.

The following examples are specific embodiments of this invention.

EXAMPLE 1

A.

3-Chloro-5-[2-(dimethylamino)ethyl]-2-phenyl-1,5-benzothiazepin-4(5H)-one, hydrochloride (1:1)

3-Chloro-2-phenyl-1,5-benzothiazepin-4(5H)-one 2,3-Dihydro-2-phenyl-1,5-benzothiazepin-4(5H)-one (25.5 grams, 0.1 mole) is stirred in 250 ml of dimethylformamide. To the stirred solution is added a solution of N-chlorosuccinimide (27 grams, 0.2 mole) in 100 ml of dimethylformamide. The mixture is stirred at 105°–110°C for 5 hours, followed by cooling. The cooled solution is poured into 1.8 liters of cold water and a solid precipitates. The crude product (28 grams) has a melting point of 238°–240°C. The crude product is crystallized from a mixture of 30 ml hot dimethylformamide and 90 ml acetonitrile yielding 26.2 grams of the title compound, melting point 241°–243°C.

B.

3-Chloro-5-[2-(dimethylamino)ethyl]-2-phenyl-1,5-benzothiazepin-4(5H)-one, hydrochloride A suspension of 3-chloro-2-phenyl-1,5-benzothiazepin-4(5H)-one (10 grams, 0.035 mole) in 140 ml of toluene is treated with powdered sodium hdyroxide (5.7 grams, 0.14 mole) and 2-dimethylaminoethyl bromide . HBr (16.8 grams, 0.072 mole). This suspension is vigorously stirred and heated on a steam bath for 30 minutes, cooled and treated with 50 ml of water. The organic phase is separated and treated with a solution of 5 ml of concentrated hydrochloric acid in 60 ml of water. The crystalline hydrochloride salt which separates is filtered to give 13.0 grams of product. Crystallization from 50 ml of isopropyl alcohol and then from 50 ml of ethanol — 300 ml of ether, yields 7.2 grams of the title compound, melting point 198°–200°C.

EXAMPLE 2

3-Chloro-5-[2-(dimethylamino)propyl]-2-phenyl-1,5-benzothiazepin-4(5H)-one, hydrochloride, hydrate A suspension of 3-chloro-2-phenyl-1,5-benzothiazepin-4(5H)-one (10 grams, 0.035 mole prepared as described in Example 1A) in 140 ml of toluene is treated with powdered sodium hydroxide (5.7 grams, 0.14 mole) and 3-dimethylaminopropyl bromide . HBr (17.8 grams, 0.072 mole). This suspension is vigorously stirred and heated on a steam bath for 30 minutes, cooled and treated with 50 ml of water. The organic phase is separated and treated with a solution of 5 ml of concentrated hydrochloric acid in 60 ml of water. The aqueous phase is separated, treated with 10 grams of potassium carbonate and the free base of the title compound is extracted with ether. The free base is dried with magnesium sulfate, filtered, and the solvent evaporated to give 11.0 grams of base. This is dissolved in 60 ml of ethanol, treated with one equivalent of hydrochloric acid in ethanol, and the solution diluted with ether until turbid. The crystalline material separates from solution and is filtered to give 8.8 grams of product, melting point 117°–120°C (sintering occurs at 105°C). Crystallization from 45 ml of acetonitrile — 90 ml of ether yields 7.5 grams of the title compound, melting point 119°–121°C (sintering occurs at 107°C).

EXAMPLE 3

A.

of dimethylformamide. To the stirred solution is added a solution of N-bromosuccinimide (35 grams, 0.2 mole) in 100 ml of dimethylformamide. The mixture is stirred at 105°–110°C for 5 hours, followed by cooling. The cooled solution is poured into 1.8 liters of cold water and a solid precipitates. The precipitate is cooled for about 16 hours, filtered, washed with water, and air-dried to yield 29.6 grams of material, melting point 190°–192°C (sintering occurs at 180°C). Crystallization of the material from a mixture of 30 ml of hot dimethylformamide and 60 ml of acetonitrile yields 17.8 grams of the title compound, melting point 240°–242°C, with decomposition.

B.

3-Bromo-5-[2-(dimethylamino)ethyl]-2-phenyl-1,5-benzothiazepin-4(5H)-one, hydrochloride, hydrate A suspension of 3-bromo-2-phenyl-1,5-benzothiazepin-4(5H)-one (5.2 grams 0.016 mole) in 65 ml of toluene is treated with powdered sodium hydroxide (2.6 grams, 0.065 mole) and 2-dimethylaminoethyl bromide . HBr (7.7 grams, 0.033 mole). This suspension is vigorously stirred and heated on a steam bath for 30 minutes, cooled and treated with 50 ml of water. The organic phase is separated and treated with a solution of 5 ml of concentrated hydrochloric acid in 60 ml of water. The solid that separates is collected, washed with a small amount of water, then with ether, and air-dried to yield 3.8 g of the title compound, melting point 207°–209°C.

EXAMPLES 4 – 8

Following the procedure of Example 1, but substituting the compound listed in column I below for 2,3-dihydro-2-phenyl-1,5-benzothiazepin-4(5H)-one and the compound listed in column II below for 2-dimethylaminoethyl bromide . HBr, the compound listed in column III is obtained.

| Example | Column I | Column II | Column III |
| --- | --- | --- | --- |
| 4 | 2,3-dihydro-7-methyl-2-phenyl-1,5-benzothiazepin-4(5H)-one | 2-methylaminoethyl bromide . HBr | 3-chloro-7-methyl-5-[2-(methylamino)ethyl]-2-phenyl-1,5-benzothiazepin-4(5H)-one hydrochloride |
| 5 | 7-ethoxy-2,3-dihydro-2-phenyl-1,5-benzothiazepin-4(5H)-one | 3-diethylaminopropyl bromide . HBr | 3-chloro-5-[3-(diethylamino)propyl]-7-ethoxy-2-phenyl-1,5-benzothiazepin-4(5H)-one, hydrochloride |
| 6 | 7-chloro-2,3-dihydro-2-phenyl-1,5-benzothiazepin-4(5H)-one | 4-dimethylaminobutyl bromide . HBr | 3,7-dichloro-5-[4-(dimethylamino)butyl]-2-phenyl-1,5-benzothiazepi 4(5H)-one, hydrochloride |
| 7 | 2,3-dihydro-2-phenyl-7-(trifluoromethyl)1,5-benzothiazepin-4(5H)-one | 3-dimethylaminopropyl bromide . HBr | 3-chloro-5-[3-(dimethylamino)propyl]-2-phenyl-7-(trifluoromethyl)-1,5-benzothiazepin-4(5H)-one, hydrochloride |
| 8 | 2,3-dihydro-7-methyl-2-phenyl-1,5-benzothiazepin-4(5H)-one | 2-(N-benzyl-N-methylamino)ethyl bromide . HBr | 5-[2-(N-benzyl-N-methylamino)ethy 3-chloro-7-methyl-2-phenyl-1,5-benzothiazepin-4(5H)-one, hydrochloride |

3-Bromo-5-[2-(dimethylamino)ethyl]-2-phenyl-1,5-benzothiazepin-4(5H)-one, hydrochloride, hydrate
3-Bromo-2-phenyl-1,5-benzothiazepin-4(5H)-one 2,3-Dihydro-2-phenyl-1,5-benzothiazepin-4(5H)-one (25.5 grams, 0.1 mole) is stirred in 250 ml

EXAMPLES 9 – 13

Following the procedure of Example 1, but substituting the compound listed in column I below for 2,3-dihydro-2-phenyl-1,5-benzothiazepin-4(5H)-one, the compound listed in column II is obtained.

| Example | Column I | Column II |
| --- | --- | --- |
| 9 | 2,3-dihydro-2-(p-methoxyphenyl)-1,5-benzothiazepin-4(5H)-one | 3-chloro-5-[2-(dimethylamino)ethyl]-2-(p-methoxyphenyl)-1,5-benzothiazepin-4(5H)-one, hydrochloride |

-continued

| Example | Column I | Column II |
|---|---|---|
| 10 | 2-(p-chlorophenyl)-2,3-dihydro-1,5-benzothiazepin-4(5H)-one | 3-chloro-2-(p-chlorophenyl)-5-[2-(dimethylamino)ethyl]-1,5-benzothiazepin-4(5H)-one, hydrochloride |
| 11 | 2,3-dihydro-2-(p-isopropylphenyl)-1,5-benzothiazepin-4(5H)-one | 3-chloro-5-[2-(dimethylamino)ethyl]-2-(p-isopropylphenyl)-1,5-benzothiazepin-4(5H)-one, hydrochlorid |
| 12 | 2,3-dihydro-2-[p-(trifluoromethyl)phenyl]-1,5-benzothiazepin-4(5H)-one | 3-chloro-5-[2-(dimethylamino)ethyl]-2-[p-trifluoromethyl)phenyl]-1,5-benzothiazepin-4(5H)-one, hydrochloride |
| 13 | 2-(p-acetylphenyl)-2,3-dihydro-1,5-benzothiazepin-4(5H)-one | 2-(p-acetylphenyl)-3-chloro-5-[2-(dimethylamino)ethyl]-1,5-benzothiazepin-4(5H)-one, hydrochloride |

EXAMPLE 14

3-Chloro-5-[2-(dimethylamino)ethyl]-2-phenyl-1,5-benzothiazepin-4(5H)-one-1-oxide, hydrochloride 3-Chloro-5-[2-(dimethylamino)ethyl]-2-phenyl-1,5-benzothiazepin-4(5H)-one, hydrochloride (prepared as described in Example 1) is treated with one equivalent of hydrogen peroxide in dilute acetic acid, and allowed to stand for about 16 hours. Solvent removal yields the title compound.

EXAMPLE 15

3-Bromo-5-[2-(dimethylamino)ethyl]-2-phenyl-1,5-benzothiazepin-4(5H)-one-1,1-dioxide, hydrochloride, hydrate 3-Bromo-5-[2-(dimethylamino)ethyl]-2-phenyl-1,5-benzothiazepin-4(5H)-one, hydrochloride, hydrate (prepared as described in Example 3) is refluxed with two equivalents of a chloroform solution of m-chloroperbenzoic acid to yield the title compound.

EXAMPLE 16

3-Chloro-5-[3-(dimethylamino)propyl]-2-phenyl-1,5-benzothiazepin-4(5H)-one, methochloride A solution of 3-chloro-5-[3-(dimethylamino)propyl]-2-phenyl-1,5-benzothiazepin-4(5H)-one (prepared as described in Example 2) in acetonitrile is treated with excess methyl chloride (3 equivalents).

After standing for 12 hours at room temperature, the solvent is evaporated to yield the title compound.

What is claimed is:

1. A compound having the formula

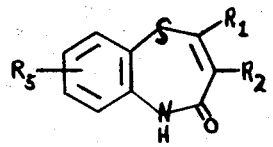

wherein $R_1$ is phenyl or substituted phenyl wherein the substitutent is selected from the group consisting of alkyl, alkoxy, halogen, trifluoromethyl or $$\text{alkyl}-\overset{\overset{\displaystyle O}{\|}}{C}-;$$

$R_2$ is chlorine or bromine and $R_5$ is hydrogen, alkyl, alkoxy, halogen or trifluoromethyl; and wherein the terms alkyl and alkoxy, in each instance employed, refer to groups having 1 to 6 carbon atoms.

2. The compound in accordance with claim 1 having the name 3-chloro-2-phenyl-1,5-benzothiazepin-4(5H)-one.

3. The compound in accordance with claim 1 having the name 3-bromo-2-phenyl-1,5-benzothiazepin-4(5H)-one.

* * * * *

UNITED STATES PATENT AND TRADEMARK OFFICE
CERTIFICATE OF CORRECTION

PATENT NO. : 3,948,889
DATED : April 6, 1976
INVENTOR(S) : John Krapcho and Chester F. Turk It is certified that error appears in the above-identified patent and that said Letters Patent are hereby corrected as shown below:

In the abstract, the third line after the formula, please omit the word "alkyl".

Column 3, line 60 should read:

-- from 0.5 mg/kg to 3 mg/kg, preferably 1 mg/kg to 2 mg/kg. The --.

Column 6, Example 6, column III, "benzothiazepi" should read --benzothiazepin--.

Column 6, Example 8, column III, "ethy" should read --ethyl]--.

*Signed and Sealed this*

Thirteenth *Day of* July 1976

[SEAL]

Attest:

RUTH C. MASON
*Attesting Officer*

C. MARSHALL DANN
*Commissioner of Patents and Trademarks*